United States Patent
Paul, Jr.

(10) Patent No.: US 8,403,979 B2
(45) Date of Patent: Mar. 26, 2013

(54) MONOCUSPID PROSTHETIC VALVE HAVING A PARTIAL SINUS

(75) Inventor: Ram H. Paul, Jr., Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 426 days.

(21) Appl. No.: 12/121,453

(22) Filed: May 15, 2008

(65) Prior Publication Data

US 2008/0288055 A1 Nov. 20, 2008

Related U.S. Application Data

(60) Provisional application No. 60/930,890, filed on May 17, 2007.

(51) Int. Cl.
*A61F 2/06* (2006.01)
(52) U.S. Cl. ...................................................... 623/1.24
(58) Field of Classification Search .................. 128/898; 623/2.36, 2.37, 2.11, 1.24, 2.12, 2.17, 900
See application file for complete search history.

(56) References Cited

U.S. PATENT DOCUMENTS

| | | | |
|---|---|---|---|
| 4,643,732 A | 2/1987 | Pietsch et al. ...................... 623/2 |
| 6,200,336 B1 | 3/2001 | Pavcnik et al. ............... 623/1.15 |
| 6,299,636 B1 | 10/2001 | Schmitt et al. .................. 623/1.2 |
| 6,299,637 B1 | 10/2001 | Shaolian et al. ............. 623/1.24 |
| 6,527,800 B1 | 3/2003 | McGuckin, Jr. et al. .... 623/1.24 |
| 6,602,286 B1 | 8/2003 | Strecker ........................ 623/1.24 |
| 7,618,447 B2 * | 11/2009 | Case et al. ..................... 623/1.26 |
| 7,628,803 B2 * | 12/2009 | Pavcnik et al. ............... 623/1.24 |
| 2003/0055492 A1 | 3/2003 | Shaolian et al. ............. 623/1.24 |
| 2003/0130726 A1 | 7/2003 | Thorpe et al. ................ 623/1.24 |
| 2004/0186558 A1 | 9/2004 | Pavcnik et al. ............... 623/1.24 |
| 2004/0225352 A1 | 11/2004 | Osborne et al. .............. 623/1.24 |
| 2004/0260389 A1* | 12/2004 | Case et al. ..................... 623/1.24 |
| 2005/0059923 A1* | 3/2005 | Gamboa ........................... 604/9 |
| 2005/0187614 A1 | 8/2005 | Agnew .......................... 623/1.24 |
| 2006/0265053 A1 | 11/2006 | Hunt .............................. 623/1.24 |
| 2007/0100435 A1* | 5/2007 | Case et al. ..................... 623/1.24 |
| 2009/0264991 A1* | 10/2009 | Paul et al. ..................... 623/1.35 |

FOREIGN PATENT DOCUMENTS

WO WO 2007/139677 12/2007

OTHER PUBLICATIONS

International Search Report dated Aug. 20, 2008 in reference to PCT Application No. PCT/US2008/063838.
PCT Written Opinion of the International Search Authority in reference to PCT Application No. PCT/US2008/063838 dated Aug. 20, 2008.

\* cited by examiner

*Primary Examiner* — David Isabella
*Assistant Examiner* — Ann Schillinger
(74) *Attorney, Agent, or Firm* — Buchanan Nipper

(57) ABSTRACT

The disclosure relates to an expandable valve prosthesis for regulating flow through a body vessel. The prosthesis comprises a frame configured to form a laterally asymmetric partial sinus and a valve member.

7 Claims, 8 Drawing Sheets ental sinuses. It is believed

MONOCUSPID PROSTHETIC VALVE HAVING A PARTIAL SINUS

PRIORITY CLAIM

This application claims the benefit of provisional U.S. Patent Application Ser. No. 60/930,890, filed May 17, 2007, which is incorporated herein by reference in its entirety.

TECHNICAL FIELD

The present disclosure relates to medical devices for implantation in a body vessel. More particularly, the present disclosure relates to intraluminal valve prostheses.

BACKGROUND OF THE INVENTION

The venous system includes a multitude of one-way bicuspid valves that permit substantially unidirectional blood to flow toward the heart. These valves are particularly important in the lower extremities to prevent the pooling of blood. When the leaflets of the bicuspid valves fail to close properly, the valve is considered "incompetent" as it permits leakage of retrograde flow resulting in the abatement of flow towards the heart.

This potentially serious condition is known as "chronic venous insufficiency." Symptoms can progress from unsightly "spider" or varicose veins to skin discoloration and painful skin ulcerations. The etiology of venous insufficiency is multifactorial, including a past history of thrombotic events, chronic venous stasis, and venous hypertension. Current treatments for venous insufficiency include elevation of the feet and compression stockings. While these can relieve symptoms, the underlying disease remains untreated. Surgical techniques are also employed in which native valves can be bypassed or replaced with autologous sections of veins having functioning valves.

Recently, various implantable medical devices and minimally invasive methods for implantation of these devices have been developed to deliver these medical devices within the lumen of a body vessel. These devices are advantageously inserted intravascularly, for example from an implantation catheter. For example, implantable medical devices can function as a replacement venous valve or aortic valve, or restore native venous or aortic valve function by bringing incompetent valve leaflets into closer proximity. Such devices can comprise an expandable frame configured for implantation in the lumen of a body vessel, such as a vein. Implantable valve devices can further comprise features that provide a valve function, such as leaflets.

However, post-implantation thrombosis and platelet deposition on surfaces of endovascular prosthetic valves may occlude the conduit defined by the endovascular prosthesis or compromise the functionality of an implanted valve by limiting the motion or responsiveness of moveable portions of the device such as valve leaflets. For example, stagnation of blood around implanted prosthetic valves may cause stiffening and thickening of valve leaflets, reducing the leaflets' functionality and possibly eventually occluding the body lumen.

In a natural valve, the leaflets are typically located within a sinus or enlargement in the vein. For example, the portion of the aorta that serves as the anchorage of the valve leaflets, or the aortic root, consists of three aortic sinuses. It is believed that the pockets formed between the leaflets and the walls of the sinus create vortices of flowing blood that help flush the pocket and prevent blood from stagnating and causing thrombosis around the valve leaflets, which can interfere with the function of the valve. It is thought that the stagnating blood prevents oxygen from reaching the endothelium covering the valve cusps, leading to hypoxia of the tissues which may explain increased thrombus formation typical in that location. Expandable-frame valve prostheses typically are of a generally cylindrical shape and lack an artificial sinus or pocket space that is sufficient for simulating these natural blood flow patterns.

SUMMARY

In one example, a valve prosthesis is provided, the prosthesis comprising an implantable frame and a valve member. The implantable frame is radially-expandable from a compressed configuration to an expanded configuration having an interior lumen. The frame defines a laterally asymmetric partial sinus portion of the interior lumen extending around between about 10% and about 90% of the circumference of the frame in the expanded configuration.

In another example, a valve prosthesis radially expandable between a compressed configuration and an expanded configuration is provided. The expanded configuration defines an interior lumen adapted to conduct fluid from an annular inlet to an outlet. The valve prosthesis comprises a frame defining a laterally asymmetric partial sinus portion of the interior lumen forming a bulge in the interior lumen extending in a first lateral direction of the frame in the expanded configuration, and a monocuspid valve leaflet having a base attached to the frame and a flexible free edge distal to the base. The free edge is movable between an open configuration permitting fluid flow through the valve orifice and a closed configuration engaging a portion of the frame opposite the partial sinus portion to reduce fluid flow through the valve orifice.

In a further example, a method of treating a venous valve-related condition by deploying a valve prosthesis within a body vessel is provided. The method comprises the steps of: 1) inserting the valve prosthesis into a body vessel in a radially compressed configuration; 2) advancing the valve prosthesis within a body vessel; 3) positioning the valve prosthesis at a point of treatment within the body vessel; and 4) expanding the valve prosthesis from the compressed configuration to an expanded configuration to deploy the valve prosthesis within the body vessel, the expanded valve prosthesis laterally distending up to one half of the circumference of the body vessel. The valve prosthesis includes a frame moveable from the compressed configuration to the expanded configuration, the frame defining an interior lumen and having a proximal end, a distal end, a luminal surface, and an abluminal surface. The frame defines a laterally asymmetric partial sinus portion of the interior lumen when the frame is in the expanded configuration. The frame further includes a means for regulating fluid flow through the interior lumen positioned within the interior lumen and being attached to the frame.

Other systems, methods, features and advantages will be, or will become, apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The medical device may be better understood with reference to the following drawings and description. The components in the figures are not necessarily to scale, emphasis

DETAILED DESCRIPTION

Figure 1:
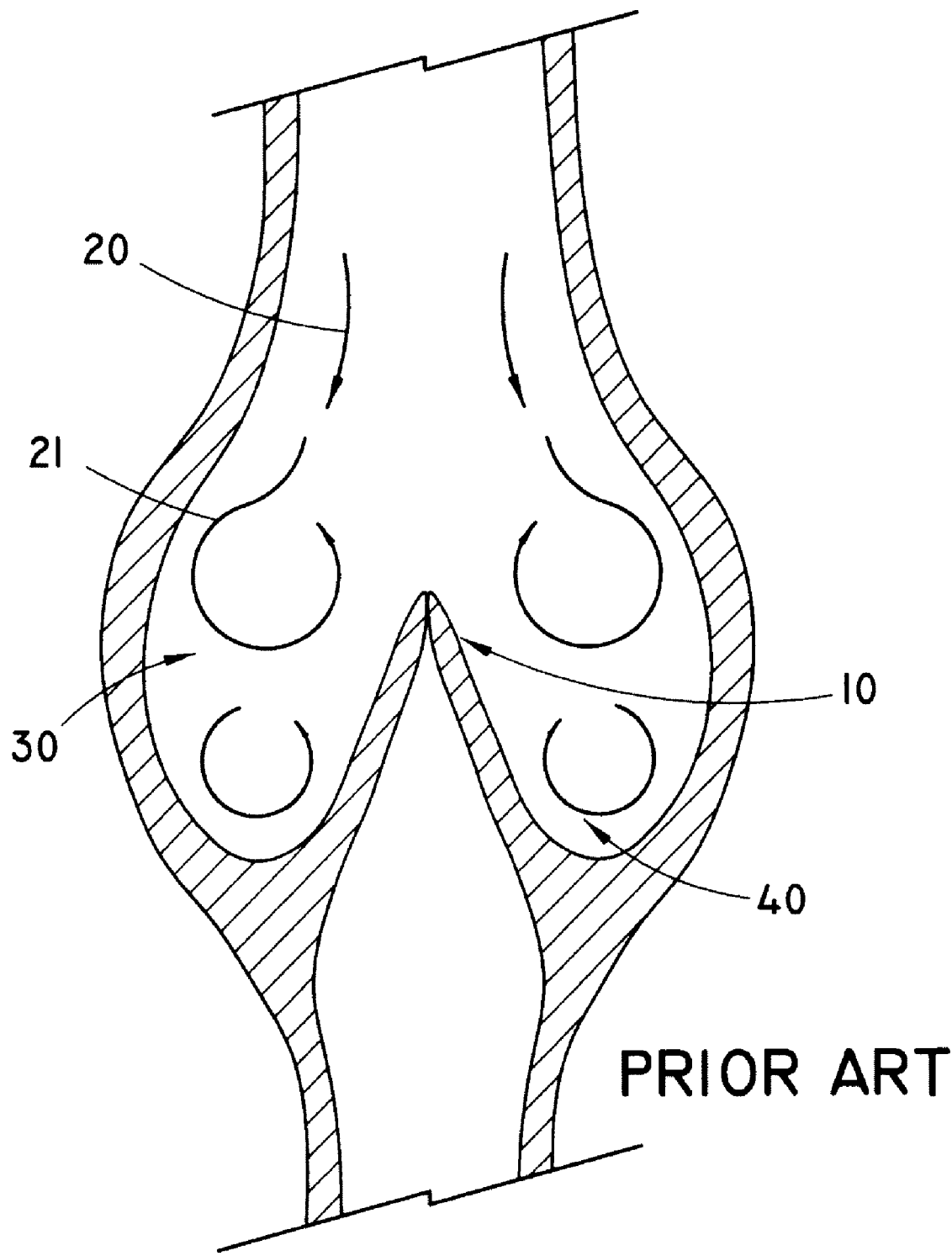
FIG. 1 depicts a cross-sectional view of a native venous valve with retrograde blood flow.

The present disclosure relates to an implantable valve prosthesis for regulating fluid flow through a body vessel. Unless otherwise defined, all technical and scientific terms used herein have the same meaning as commonly understood by one of ordinary skill in the art to which this disclosure pertains. In case of conflict, the present document, including definitions, will control. Preferred methods and materials are described below, although methods and materials similar or equivalent to those described herein can be used in the practice or testing of the present disclosure. All publications, patent applications, patents and other references mentioned herein are incorporated by reference in their entirety. The materials, methods, and examples disclosed herein are illustrative only and not intended to be limiting.

DEFINITIONS

The term "implantable" refers to an ability of a medical device to be positioned at a location within a body, such as within a body lumen.

The term "frame" is used herein to refer to a structure that can be implanted, or adapted for implantation, within the lumen of a body vessel.

As used herein, the term "body vessel" means any tube-shaped body passage lumen that conducts fluid, including but not limited to blood vessels such as those of the human vasculature system, esophageal, intestinal, billiary, urethral and ureteral passages.

The term "alloy" refers to a substance composed of two or more metals or of a metal and a nonmetal intimately united, for example by chemical or physical interaction. Alloys can be formed by various methods, including being fused together and dissolving in each other when molten, although molten processing is not a requirement for a material to be within the scope of the term "alloy." As understood in the art, an alloy will typically have physical or chemical properties that are different from its components.

The terms "about" or "substantially" used with reference to a quantity includes variations in the recited quantity that are equivalent to the quantity recited, such as an amount that is insubstantially different from a recited quantity for an intended purpose or function.

"Proximal" means that position or portion of a component which is closest to the patient's heart.

"Distal" means that position of portion of a component which is furthest from the patient's heart.

"Antegrade fluid flow" refers to the flow of fluid in a primary direction of normal movement within a body vessel. For example, in the venous system, antegrade fluid flow proceeds primarily toward the heart.

"Retrograde fluid flow" refers to fluid flow in a direction opposite the primary (antegrade) direction of fluid flow. For example, in the venous system, retrograde fluid flow is primarily directed away from the heart.

The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

Valve Prosthesis

Valve prostheses may be any medical device that is introduced temporarily or permanently into the body for the prophylaxis or therapy of a medical condition. For example, such valve prostheses may include, but are not limited to, heart valve prostheses, venous valve prostheses, artificial organs such as artificial hearts, and ventricular assist devices. Typical subjects (also referred to herein as "patients") are vertebrate subjects (i.e., members of the subphylum cordata), including, mammals such as cattle, sheep, pigs, goats, horses, dogs, cats and humans. Valve prostheses according to the present disclosure preferably comprise a frame having a partial sinus and at least one monocuspid valve member.

Frame

In the examples depicted, for example FIGS. 2-6, the frame is configured such that when the device is deployed within the body vessel, an artificial partial sinus is formed adjacent the monocuspid valve member such that bodily fluids, for example blood, collecting within the pocket formed around the base of the valve member are more likely to be flushed out on a continual basis due to the advantageous geometry created by the valve member and artificial partial sinus.

This principle is illustrated in the example of FIG. 1 which shows a natural venous valve 10 in which retrograde blood 20 flowing or falling back down and closing the valve is thought to create a series of vortices 21 as it contacts the leaflets. It is believed that the rounded shape of the enlarged natural sinus 30 surrounding the valve 10 facilitates creation of these vortices, thereby preventing blood from pooling or stagnating within the pockets 40 at the base of the valve 10, which may lead to thrombus formation or other problems.

Figure 2:
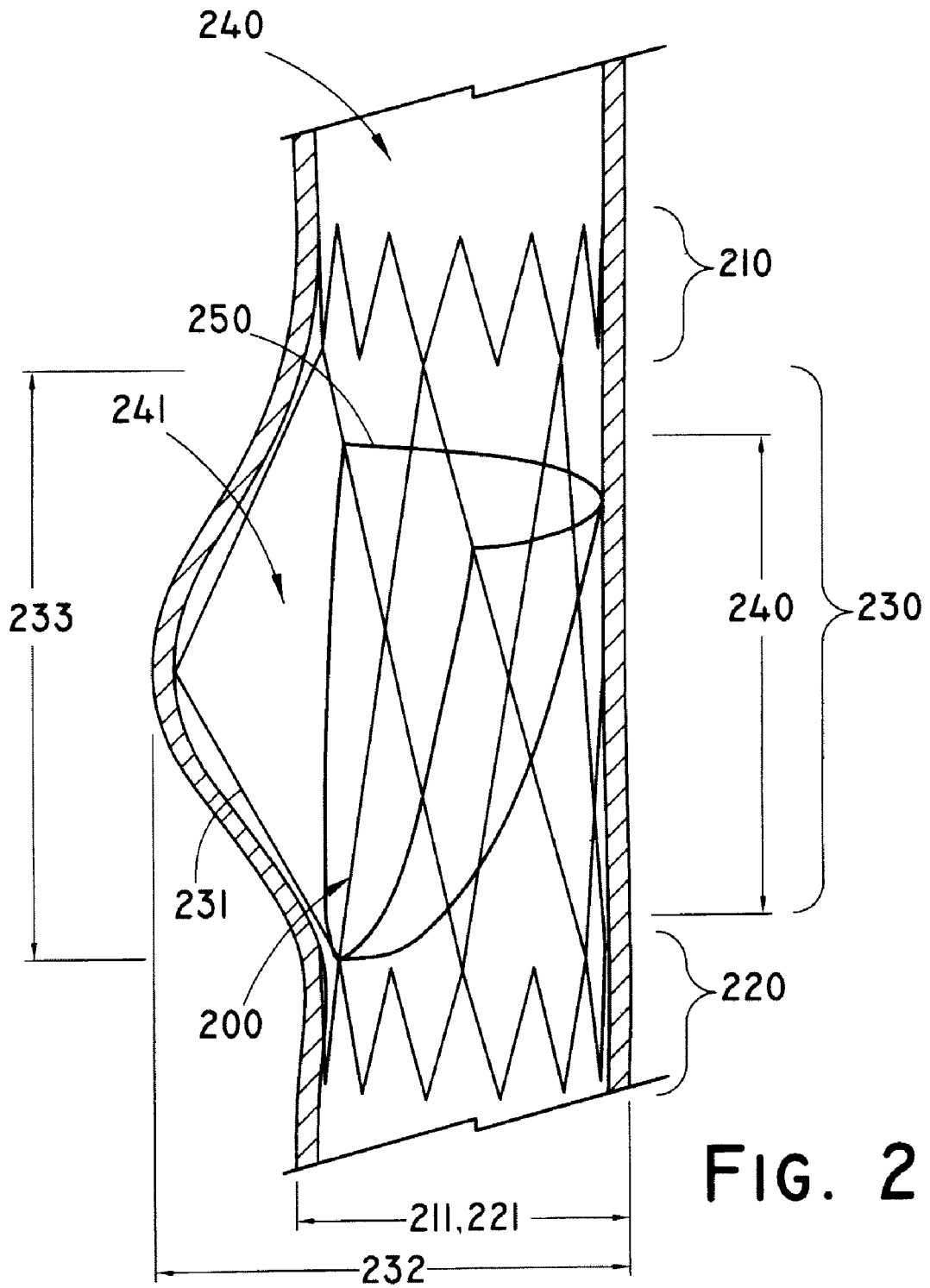
FIG. 2 depicts a side view of a prosthetic valve in a body vessel comprising a frame having a partial sinus according to one example.
Figure 3A:
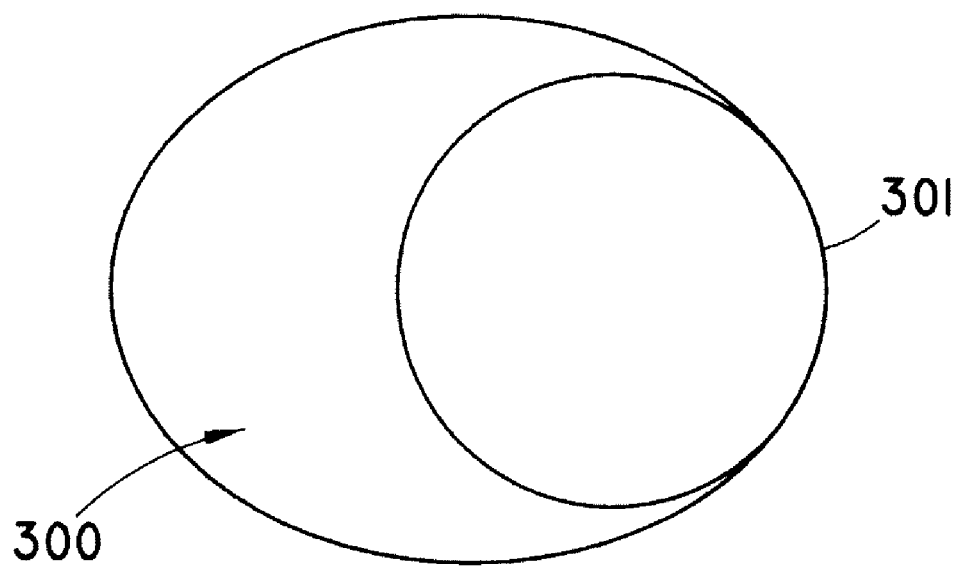
FIGS. 3A and 3B depict top views a prosthetic valve in a body vessel comprising a frame having a partial sinus.
Figure 3B:
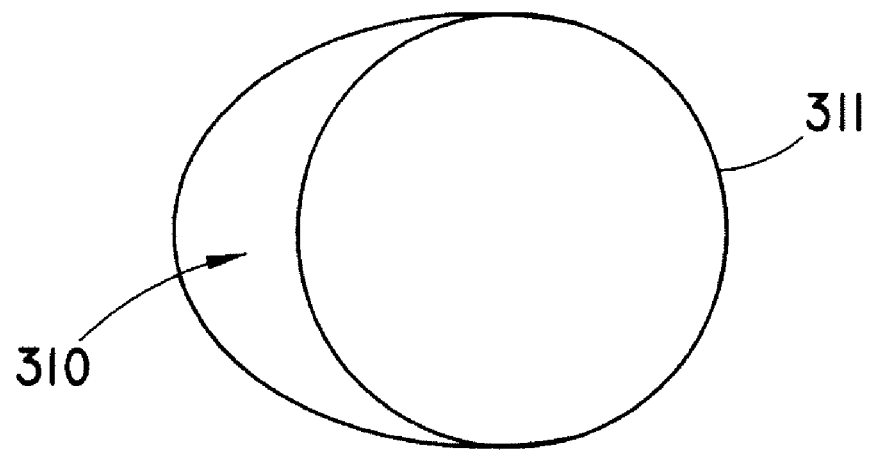

The frame preferably defines an interior lumen including an artificial partial sinus and includes a means for regulating fluid flow through the interior lumen. The means for regulating fluid flow is preferably a valve member that beneficially improves the venous valve function served by the natural sinus in the vascular system. For example, FIG. 2 depicts a side view of an exemplary prosthesis in which the frame 200 defines an interior lumen.

The frame 200 includes a first or proximal section 210 and a second or distal section 220 that are spaced apart from one another, defining an intermediate section 230 for creating the artificial partial sinus 241 in the body vessel 240. The artificial partial sinus 241 is a laterally asymmetric portion of the interior lumen defined by the intermediate section 230 of the frame 200. The intermediate section 230 includes an expanded portion 231, having a larger diameter 232 than the diameter 211, 221 of the proximal 210 and distal 220 portions, respectively, of the frame 200, that upon deployment, creates the artificial partial sinus 241 adjacent the valve member 250. In the expanded frame configuration, the distal frame portion 220 and/or proximal frame portion 210 are preferably annular structures (e.g., having circular or elliptical lateral cross-sections). In one example, the distal frame portion 220 and/or proximal frame portion 210 have a radial force less than the radial force of the intermediate portion 230, thereby allowing the distal and/or proximal frame portions 210, 220 to more compliant to vessel movement than the intermediate portion 230.

The intermediate portion 230 of the frame 200 defining the partial sinus 241 portion of the interior lumen is preferably characterized by a greater lateral distance between the frame 200 and the longitudinal axis of the proximal 210 or distal 220 portions than the frame 200 in the direction of the partial sinus 241 than in the opposite lateral direction. The partial sinus preferably has a longitudinal length 233 that is at least as great as the longitudinal length 240 of the valve member 250. The partial sinus 241 is preferably formed by a bulge in the luminal surface of the frame 200 extending away from the interior lumen. The partial sinus extends around between about 5% and about 90% the circumference of the interior lumen; between about 10% and about 75% around the circumference of the interior lumen; and between about 25% and about 60% around the circumference of the interior lumen. In one example, depicted in FIG. 3A, the partial sinus 300 may extend around up to about 75% of the circumference of the frame 301. In a further example, shown in FIG. 3B, the partial sinus 310 may extend around up to about 50% of the circumference of the frame 311.

The configuration of the partial sinus may depend on several factors, including body vessel diameter, valve member geometry such as length, slack, and orientation, fluid column pressures at the site of deployment, and other factors. For example, the partial sinus may have a longitudinal length at least as great as the longitudinal length of the valve member, permitting the valve member to fully retract within the partial sinus, thereby substantially uninterrupting antegrade flow.

Figure 4:
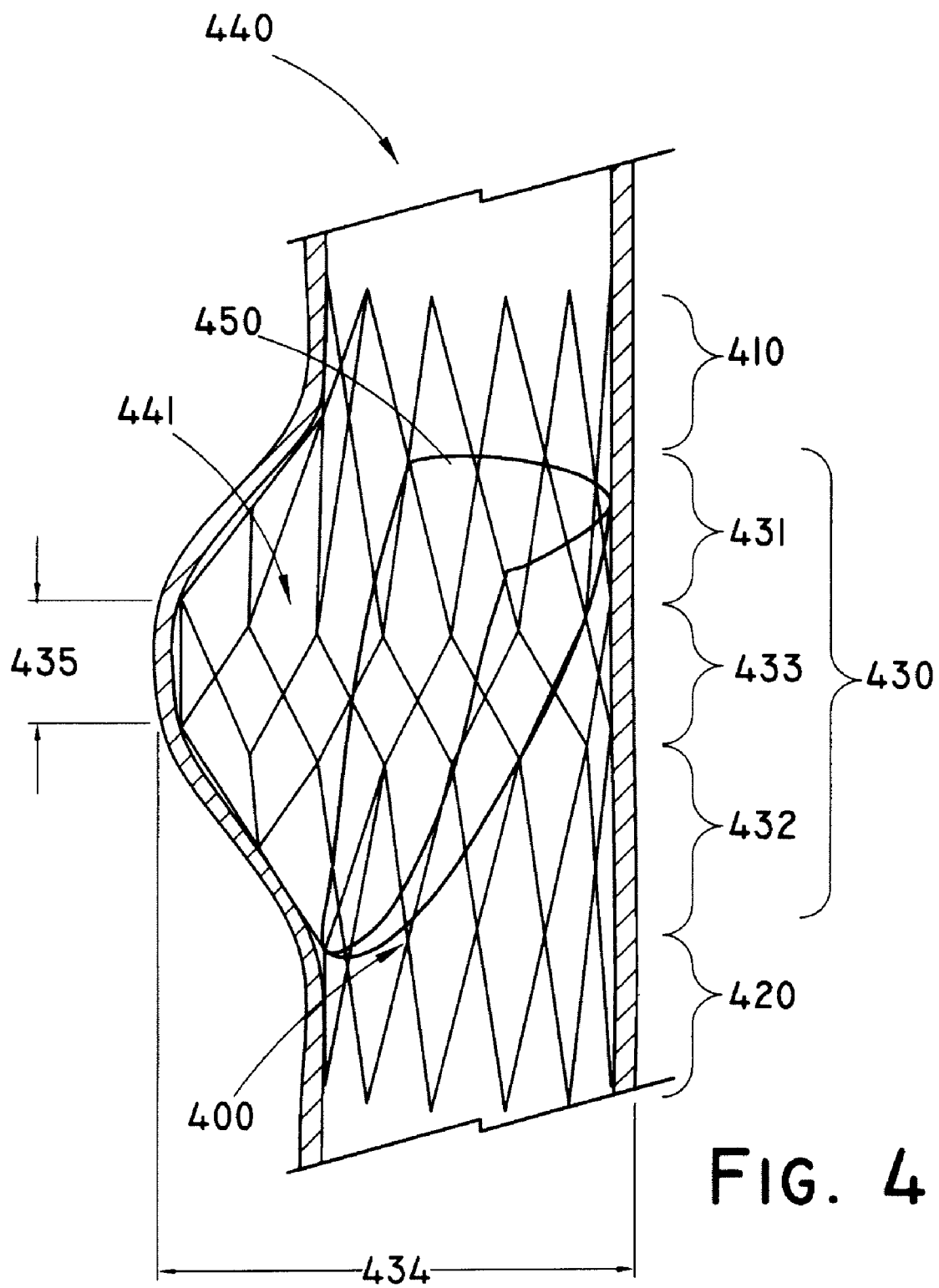
FIG. 4 depicts a side view of a prosthetic valve in a body vessel comprising a frame having a partial sinus according to a second example.
Figure 5:
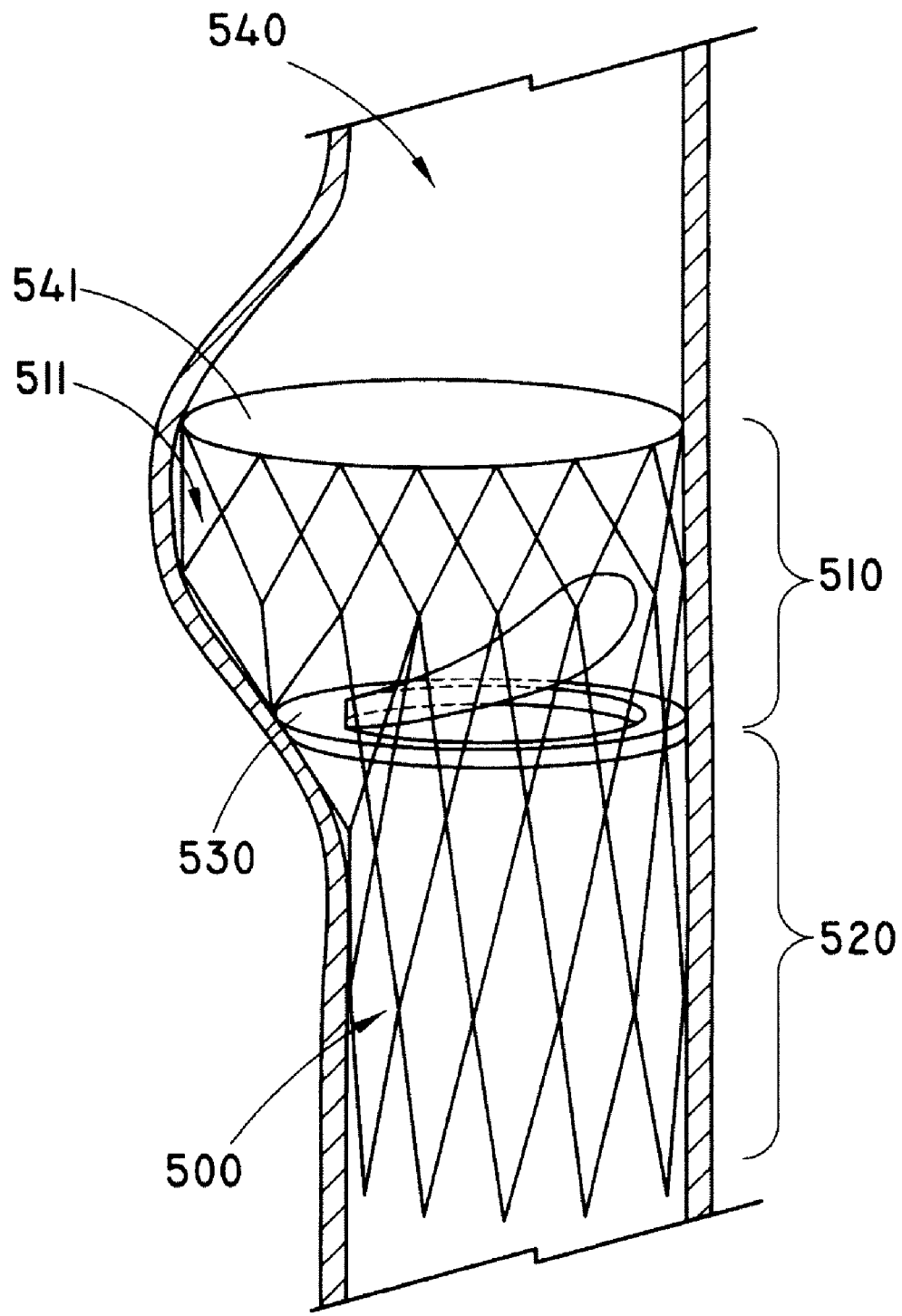
FIG. 5 depicts a side view of a prosthetic valve frame comprising a partial sinus according to another example.
Figure 6:
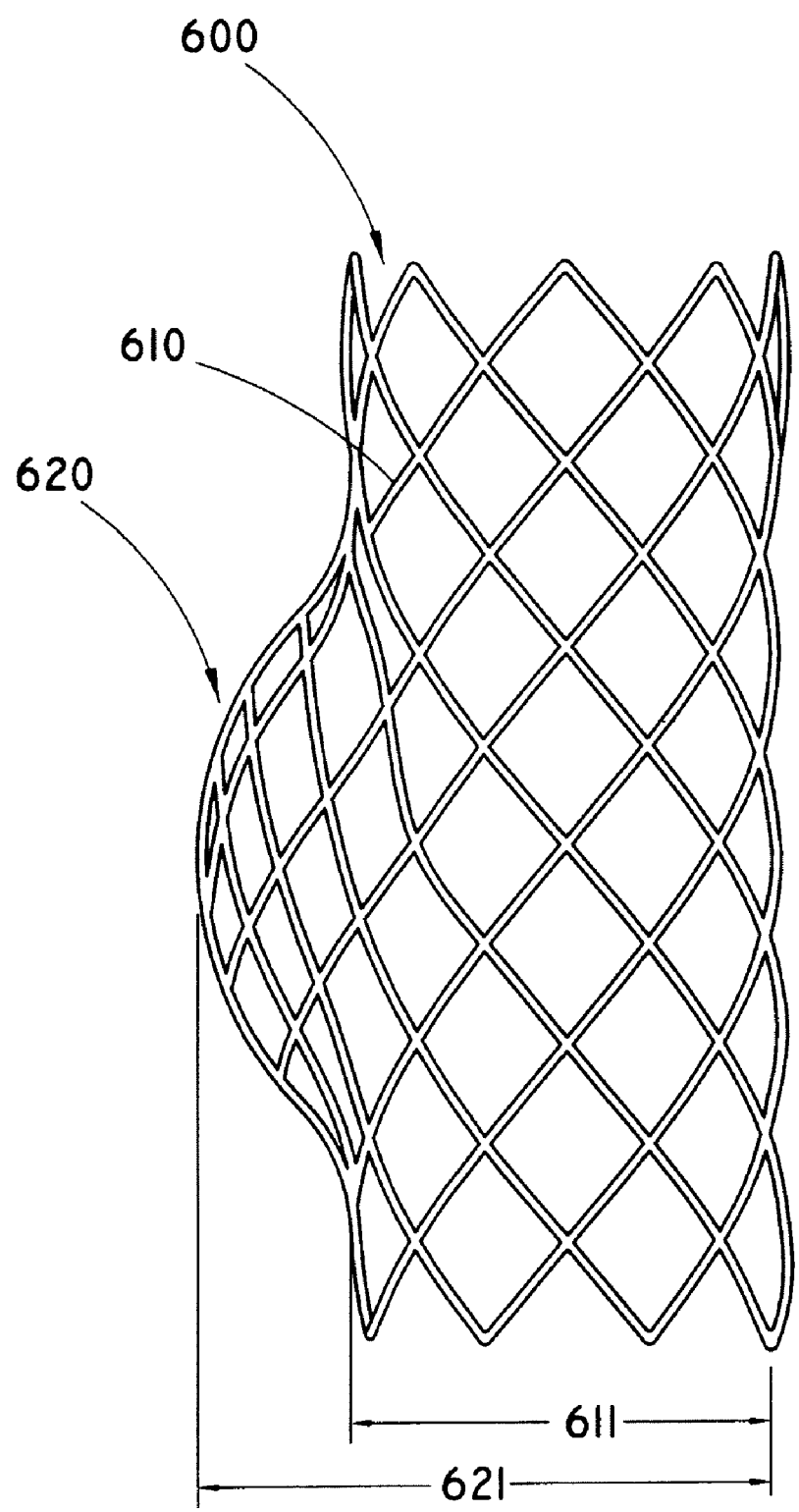
FIG. 6 depicts a side view of a prosthetic valve frame comprising a partial sinus according to a further example.

Further methods of creating a partial sinus are depicted in FIGS. 4-6. FIG. 4 depicts another method of creating an artificial partial sinus, whereby the frame 400 includes a first or proximal section 410 and a second or distal section 420 that are spaced apart from one another, defining an intermediate section 430 for creating the artificial partial sinus 441 adjacent the valve member 450 in the body vessel 440. The intermediate section 430 comprises a first 431, a second 432, and a third 433 intermediate subsection. The third intermediate subsection 433, located between intermediate subsection 431 and 432, extends the length of the artificial partial sinus. The illustrative third intermediate subsection 433 has a width 434 and height 435 that can be adjusted to create the desired geometry of the artificial partial sinus 441. Additional subsections may be added as well if desired.

In the example of FIG. 5, the expanded frame portion 511, which comprises the proximal section 510 of the frame 500, includes a flared configuration that extends laterally outward in one direction from the distal section 520 (no separately functional intermediate section is present). The proximal section 510 includes a portion of the frame 500 defining a laterally asymmetric portion of an interior lumen, extending away from up to half the circumference of the distal section 520. A means for regulating fluid flow may be positioned within the interior lumen. For example, valve member 530 may be attached about the proximal end 510, while the flared, expanded portion 511 thereabout causes the vessel 540 to bulge outward, thus creating an artificial partial sinus 541 about the proximal end of the frame 510. The artificial partial sinus 541 comprises a combination of a supported and an unsupported portion in the example of FIG. 5.

Though the illustrative examples depict frames comprising portions having a serpentine or "zig-zag" configuration that are attached to one another, for example by feeding sutures through the apices of adjoining bends and securing it therearound, the frame may have any possible configuration. For example, the frame may comprise a mesh or web of interconnecting struts, a wire based frame, and a partially radially compliant frame capable of dynamic adjustability or dynamic movement in response to external forces, such as changes in the dimensions of the lumen of the body vessel. The radial compliance of the frame refers to the resistance of the frame to a radial force applied to the abluminal surface of the frame toward the center of the interior lumen.

FIG. 6 illustrates a frame 600 comprising a tubular mesh 610 of interconnecting struts configured such that a portion 620 of the mesh has a diameter 621 greater than the remaining mesh structure diameter 611. This expanded portion 620 defines a bulge in the interior lumen that extends about 50% around the circumference of the frame 600, though in further examples the bulge may extend between about 5% and about 90% around the circumference of the frame; between about 10% and about 75% around the circumference of the frame; and between about 25% and about 60% around the circumference of the frame. The expanded portion 620 typically resembles a laterally asymmetric bulge in the frame 600 and may be created, for example, by heat setting the frame 600 on a mandrel having the desired final shape.

Suitable frames may be made from one or more suitable materials and need only be biocompatible or able to be made biocompatible. Examples of suitable materials include, without limitation, stainless steel, nitinol, nickel titanium alloy, nonmagnetic nickel-cobalt-chromium-molybdenum alloy, gold, tantalum, platinum or platinum iridium, niobium, tungsten, iconel, ceramic, nickel, titanium, stainless steel/titanium composite, cobalt, chromium, cobalt/chromium alloys, magnesium, aluminum, or other biocompatible metals and/or composites or alloys such as carbon or carbon fiber, cellulose acetate, cellulose nitrate, silicone, cross-linked polyvinyl alcohol (PVA) hydrogel, cross-linked PVA hydrogel foam, polyurethane, polyamide, styrene isobutylene-styrene block copolymer (Kraton), polyethylene teraphthalate, polyurethane, polyamide, polyester, polyorthoester, polyanhydride, polyether sulfone, polycarbonate, polypropylene, high molecular weight polyethylene, polytetrafluoroethylene, or other biocompatible polymeric material, or mixture of copolymers thereof; polyesters such as, polylactic acid, polyglycolic acid or copolymers thereof, a polyanhydride, polycaprolactone, polyhydroxybutyrate valerate or other biodegradable polymer, or mixtures or copolymers thereof; extracellular matrix components, proteins, collagen, fibrin or other therapeutic agent, or mixtures thereof. Desirably, the frame material includes stainless steel or nitinol.

In some examples, the frame itself, or any portion of the frame, may comprise one or more metallic bioabsorbable materials. Suitable metallic bioabsorbable materials include magnesium, titanium, zirconium, niobium, tantalum, zinc and silicon and mixtures and alloys. For example, a zinc-titanium alloy such as discussed in U.S. Pat. No. 6,287,332 to Bolz et al., which is incorporated herein by reference in its entirety, can be used. The metallic bioabsorbable material can further contain lithium, sodium, potassium, calcium, iron and manganese or mixtures thereof. For example, an alloy containing lithium:magnesium or sodium:magnesium can be used. The physical properties of the frame can be controlled by the selection of the metallic bioabsorbable material, or by forming alloys of two or more metallic bioabsorbable materials. For example, when 0.1% to 1%, percentage by weight, titanium is added to zinc, the brittle quality of crystalline zinc can be reduced. In another example, when 0.1% to 2%, percentage by weight, gold is added to a zinc-titanium alloy, the grain size of the material is reduced upon cures and further and the tensile strength of the material increases.

The frame can comprise a bioabsorbable material that can be degraded and absorbed by the body over time to advantageously eliminate a frame or portion thereof from the vessel before, during or after the remodeling process. A number of bioabsorbable homopolymers, copolymers, or blends of bioabsorbable polymers are known in the medical arts. These include, but are not necessarily limited to, polyesters, poly(amino acids), copoly(ether-esters), polyalkylenes oxalates, polyamides, poly(iminocarbonates), polyorthoesters, polyoxaesters, polyamidoesters, polyoxaesters containing amido groups, poly(anhydrides), polyphosphazenes, poly-alpha-hydroxy acids, trimethlyene carbonate, poly-beta-hydroxy acids, polyorganophosphazines, polyanhydrides, polyesteramides, polyethylene oxide, polyester-ethers, polyphosphoester, polyphosphoester urethane, cyanoacrylates, poly(trimethylene carbonate), poly(iminocarbonate), polyalkylene oxalates, polyvinylpyrolidone, polyvinyl alcohol, poly-N-(2-hydroxypropyl)-methacrylamide, polyglycols, aliphatic polyesters, poly(orthoesters), poly(ester-amides), polyanhydrides, modified polysaccharides and modified proteins.

Some specific examples of bioabsorbable materials include polymers and co-polymers comprising a polylactic acid, a polyglycolic acid, a polycaprolactone or derivatives thereof. Suitable bioabsorbable materials for a frame include: poly(epsilon-caprolactone), poly(dimethyl glycolic acid), poly(hydroxy butyrate), poly(p-dioxanone), polydioxanone, PEO/PLA, PLA, poly(lactide-co-glycolide), poly(hydroxybutyrate-co-valerate), poly(glycolic acid-co-trimethylene carbonate), poly(epsilon-caprolactone-co-p-dioxanone), poly-L-glutamic acid or poly-L-lysine, polylactic acid, polylactide, polyglycolic acid, polyglycolide, poly(D,L-lactic acid), L-polylactic acid, poly(glycolic acid), polyhydroxyvalerate, cellulose, chitin, dextran, fibrin, casein, fibrinogen, starch, collagen, hyaluronic acid, hydroxyethyl starch, and gelatin. A frame may also comprise one or more naturally derived bioabsorbable polymers, including modified polysaccharides such as cellulose, chitin, and dextran or modified proteins such as fibrin and casein.

Preferably, the frame can have a compressed and an expanded configuration. In some aspects, the expanded configuration can be resiliently further extended in one or more radial directions. In some aspects, a frame can expand from a compressed, or unexpanded, delivery configuration to one or more radially expanded deployment configurations, for example through self-expansion or balloon expansion of the frame. The expanded configuration can have any suitable cross-sectional configuration, including circular or elliptical. In one example, the frame can be oriented along the longitudinal axis of a body vessel in the expanded or compressed configurations.

In one example, the frame is self-expanding. Upon compression, self-expanding frames can expand toward their pre-compression geometry. In some examples, a self-expanding frame can be compressed into a low-profile delivery conformation and then constrained within a delivery system for delivery to a point of treatment in the lumen of a body vessel. At the point of treatment, the self-expanding frame can be released and allowed to subsequently expand to another configuration.

In other examples the frames may not be self-expanding. For example, frames may be balloon expandable.

The dimensions of the implantable frame will depend on its intended use. Typically, the collapsed dimension of the frame will usually be in the range from about 1 mm to 10 mm, more usually being in the range from 1.5 mm to 6 mm for vascular applications. The expanded dimension will usually be in the range from about 2 mm to 30 mm, preferably being in the range from about 2.5 mm to 18 mm for vascular applications.

Also provided are examples wherein the frame comprises a means for orienting the frame within a body lumen. For example, the frame can comprise a marker, such as a radiopaque portion of the frame that would be seen by remote imaging methods including X-ray, ultrasound, Magnetic Resonance Imaging and the like, or by detecting a signal from or corresponding to the marker. The radiopaque indicia may be used to radially or circumferentially orient the valve, such as to orient the partial sinus along the long axis of the vein. In other examples, the delivery device can comprise a frame with indicia relating to the orientation of the frame within the body vessel. In other examples, indicia can be located, for example, on a portion of a delivery catheter that can be correlated to the location of the frame within a body vessel.

A frame or delivery device may comprise one or more radiopaque materials to facilitate tracking and positioning of the medical device, which may be added in any fabrication method or absorbed into or sprayed onto the surface of part or all of the medical device. The degree of radiopacity contrast can be altered by implant content. Radiopacity may be imparted by covalently binding iodine to the polymer monomeric building blocks of the elements of the implant. Common radiopaque materials include barium sulfate, bismuth subcarbonate, and zirconium dioxide. Other radiopaque elements include: cadmium, tungsten, gold, tantalum, bismuth, platinum, iridium, and rhodium. In one preferred example, iodine may be employed for its radiopacity and antimicrobial properties. Radiopacity is typically determined by fluoroscope or x-ray film.

Valve Members

Prosthetic valves comprise a means for regulating fluid flow through an interior lumen defined by at least a portion of an implantable frame. For example, at least one valve member may be attached to the frame to form a prosthetic valve. Prosthetic valves comprising at least one valve member can be used to regulate fluid flow in a vein, for example to treat venous valve incompetency. One or more prosthetic valves comprising one or more valve members can be implanted in a vein with incompetent native venous valves so as to provide a valve to replace the incompetent native valves therein.

Monocuspid valve members may allow for a larger artificial partial sinus and increased flushing about the valve member. Further, a monocuspid valve member may be positioned at least partially within the partial sinus such that antegrade fluid flow is substantially unimpeded. For example, a monocuspid valve member may comprise a leaflet having a free edge responsive to the flow of fluid through the body vessel. A "free edge" refers to a portion of a leaflet that is not attached to the prosthetic valve, but forms a portion of a valve orifice. Preferably a leaflet free edge is a portion of the edge of the leaflet that is free to move in response to the direction of fluid flow in contact with the leaflet.

Figure 7:
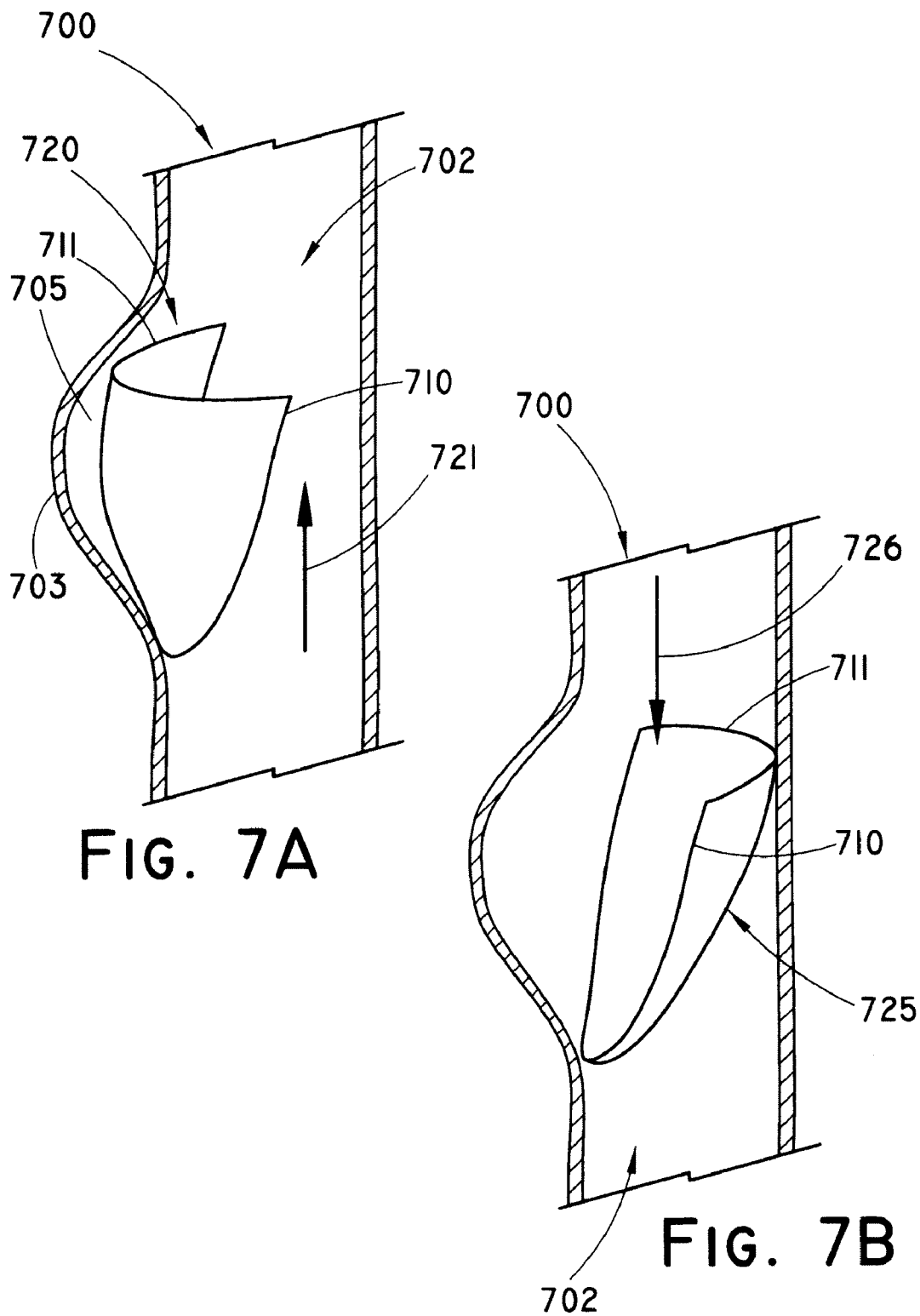
FIGS. 7A and 7B depict side views of a prosthetic valve monocuspid valve member according to one example.

For example, FIGS. 7A and 7B illustrate partial cut-aways (i.e., the frame is not depicted) of a prosthetic valve in a body vessel 700, exposing a valve member comprising a single leaflet 710 with a free edge 711. The leaflet 710 is moveable between first 720 and second 725 positions when the prosthesis is placed within a body vessel 700. In the first position 720, illustrated in FIG. 7A, the leaflet 710 permits fluid flow in a first direction, represented by arrow 721, to flow through the vessel 700. The pressure created by the flow of fluid exerts a force on one face of the leaflet 710, forcing it toward the vessel wall 703.

In one example, the partial sinus 705 may permit the leaflet 710 to be positioned at least partially within the partial sinus 705 when in the first position 720 such that antegrade fluid 721 flow is substantially unimpeded. Further, the leaflet 710 may have a curvature approximating the curvature of the partial sinus 705 to further enhance the ability of the leaflet 710 to be positioned within the partial sinus 705 when in the first position 720.

In the second position 725, illustrated in FIG. 7B, the leaflet 710 substantially prevents fluid flow in a second, opposite direction, represented by arrow 726 from flowing through the prosthesis vessel 700. Flow in the second opposite direction 726 is commonly referred to as retrograde flow. The leaflet 710 moves to the second position 725 when a pressure change and/or reversal of flow direction exerts a force on an opposite face of the leaflet 710 and forces the leaflet 710 away from the vessel wall 703 and across the lumen 702 of the vessel 700. The first position 720 of the leaflet 710 can be considered an open position, and the second position 725 can be considered a closed position. By moving between these two positions, the leaflet 710 provides a valving function to the vessel 700 allowing it to regulate fluid flow through the vessel 700. The degree to which the valve opens to the first position 720 may be varied, for example by adjusting the amount of tension, or slack, built into the leaflet 710. For example, a tauter leaflet may only open halfway such that the free edge bisects the vessel opening, particularly if there is less tension across the bottom portion of the leaflet. Preferably, in the first position 720, at least the leaflet free edge 711 is permitted to retract within the partial sinus to aid in fluid flow and fluid flushing about the valve member.

Figure 8:
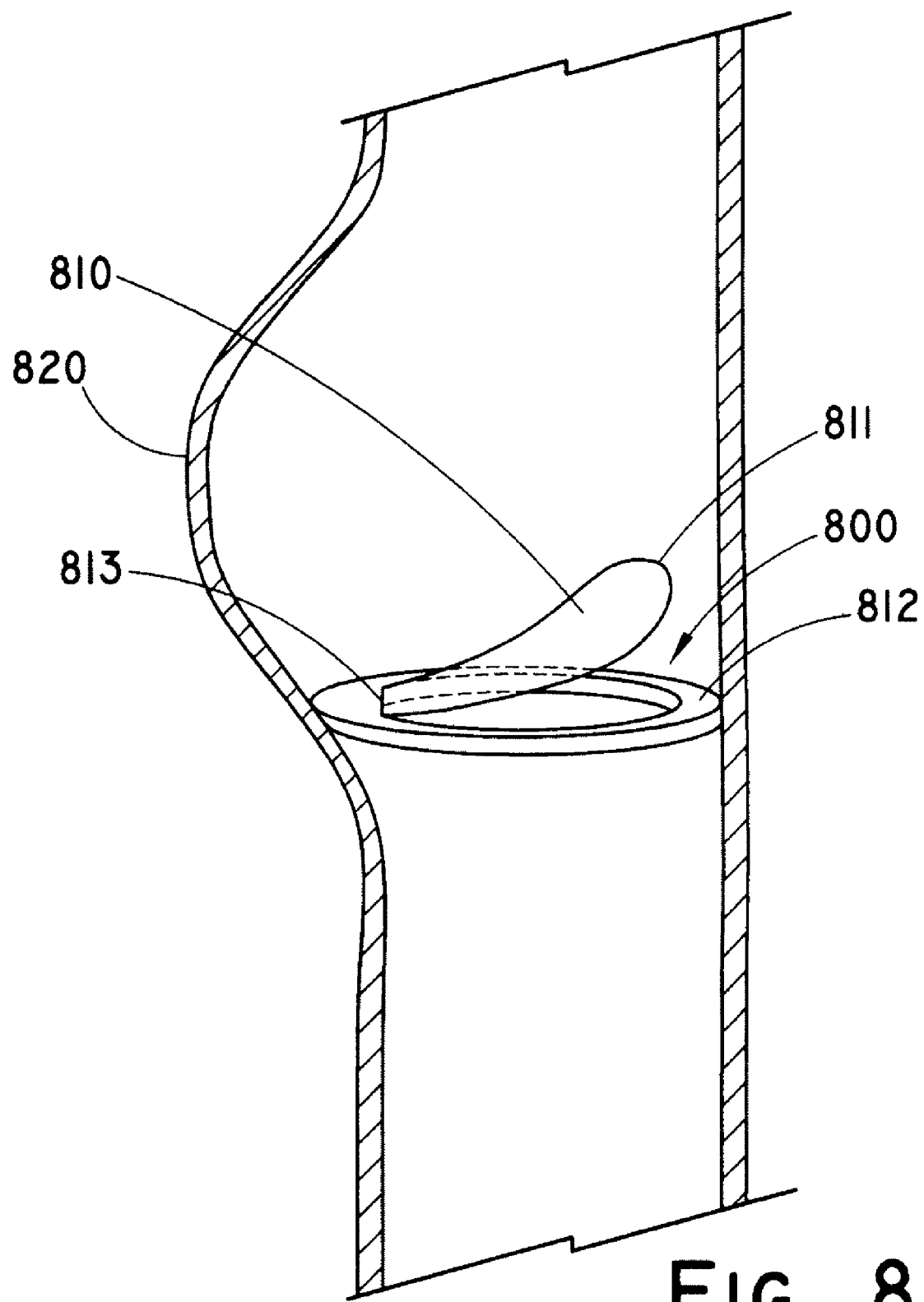
FIG. 8 depicts a side view of a prosthetic valve monocuspid valve member according to a second example.

FIG. 8 depicts a cut-away (i.e., the frame is not depicted) of another example of a monocuspid valve prosthesis, wherein the valve prosthesis comprises an interior lumen including a partial sinus region 820 and valve member 800 positioned within the interior lumen. The valve member 800 comprises a single leaflet 810 with a free edge 811. The leaflet 810 is mounted on a leaflet seat 812 and is operatively connected to the leaflet seat 812 via a hinge 813 allowing the leaflet 810 to move freely in response to flow. The valve member 800 sealably engages the leaflet seat 812 to prevent retrograde fluid flow through the interior lumen. Fluid flow in the antegrade direction displaces the valve member 800 away from the leaflet seat 812 toward the partial sinus region 820. In one example, the partial sinus 820 may permit the valve leaflet 810 to be positioned at least partially within the partial sinus 820 when in an open position such that antegrade fluid flow is substantially unimpeded. Further, the leaflet 810 may have a curvature approximating the curvature of the partial sinus 820 to further enhance the ability of the leaflet 810 to be positioned within the partial sinus 820 when in the open position.

A wide variety of materials acceptable for use as leaflets are known in the art, and any suitable material can be utilized. The material chosen need only be able to perform as described herein, and be biocompatible, or able to be made biocompatible. Examples of suitable materials include natural materials, and synthetic materials.

Examples of suitable natural materials include collagen and extracellular matrix (ECM) material, such as submucosa. The "extracellular matrix" is typically a collagen-rich substance that is found in between cells in animal tissue and serves as a structural element in tissues. Such an extracellular matrix is preferably a complex mixture of polysaccharides and proteins secreted by cells. The extracellular matrix can be isolated and treated in a variety of ways. Following isolation and treatment, it is referred to as an ECM. ECM may be isolated from submucosa (including small intestine submucosa), stomach submucosa, urinary bladder submucosa, tissue mucosa, renal capsule, dura mater, liver basement membrane, pericardium or other tissues. One specific example of ECM is small intestine submucose (SIS). When implanted, SIS can undergo remodeling and can induce the growth of endogenous tissues upon implantation into a host. SIS has been used successfully in vascular grafts, urinary bladder and hernia repair, replacement and repair of tendons and ligaments, and dermal grafts. SIS is particularly well-suited for use as valve members, such as leaflets.

In addition to xenogenic biomaterials, such as SIS, autologous tissue can be harvested as well. Additionally Elastin or Elastin Like Polypetides (ELPs) and the like offer potential as a material to fabricate the flexible covering or discrete shaping members to form a device with exceptional biocompatibility. Another alternative is use of allographs such as harvested native valve tissue. Such tissue is commercially available in a cryopreserved state.

In one aspect, the valve member, and preferably a valve leaflet, is formed from explanted biological tissue, such as aortic tissue, that is treated in a manner that improves the biocompatibility of the tissue for an intended use. For example, the tissue may be treated to improve resistance to post-implantation mineralization. One preferred method is described in U.S. Pat. No. 5,595,571 (Filed Apr. 18, 1994), incorporated by reference herein in its entirety, which involves exposing biological material including cellular and non-cellular structural components to a buffered solution having a pH in the range from about 5.0 to about 8.0 and a temperature in the range from about 12° C. to about 30° C. for a sufficient amount of time to facilitate the degradation of cells by autolytic enzymes within the cells, whereby at least one region of the biological material is rendered substantially acellular while preserving the overall structural integrity and non-cellular structural components of the biological material The exposure occurs prior to any fixation of the biological material. Other suitable tissue treatments are described in the following references, all of which are incorporated herein by reference in their entirety: U.S. Pat. No. 5,720,777, U.S. Pat. No. 5,843,180 and U.S. Pat. No. 5,843,181 (Biological Material Pre-fixation Treatment); U.S. Pat. No. 4,798,611 (Enhancement of Xenogeneic Tissue by treatment with glutaraldehyde and then irradiation); U.S. Pat. No. 4,813,958 (Crosslinked anisotropic mammalian diaphragm in surgical reconstruction); U.S. Pat. No. 3,966,401 (Tissue for Implantation so as to Provide Improved Flexibility by Tissue subjecting tissue to tanning fluid when under pressure until the tissue assumes a natural configuration during tanning in Tanning fluids including 4% formaldehyde and 2% glutaraldehyde); U.S. Pat. No. 4,800,603 (Tissue Fixation with Vapor by subjecting tissue to a vapor of a fixative while the tissue is unstressed); and U.S. Pat. No. 4,813,964 and U.S. Pat. No. 4,813,958 (Crosslinked anisotropic xenogeneic diaphragm tissue in flexor tendon pulley reconstruction, such as a method of tissue replacement for nonfunctional flexor tendon pulleys including replacing the flexor tendon pulleys with anisotropic, crosslinked mammalian, bovine or porcine diaphragm which is characterized in that the diaphragm has one smooth side and one fibrous side, the smooth side being placed against the flexor tendon). Preferably, the explanted tissue explanted tissue is pre-treated by performing at least one of the following steps: maintaining the explanted tissue at a pH in the range from about 5.0 to about 8.0 and a temperature in the range from about 12° C. to about 30° C. for a sufficient amount of time sufficient to effect the degradation of at least a portion of the cells by autolytic enzymes within the cells; contacting the explanted tissue with a chemical cross-linking agent and then irradiating with X-ray or gamma radiation; contacting the explanted tissue with a tanning fluid including formaldehyde or glutaraldehyde; or placing tissue explanted tissue within an atmosphere of substantially unpressurized vapor of containing glutaraldehyde, and maintaining the tissue within the atmosphere of substantially unpressurized vapor in a manner sufficient to provide substantially uniform application of the fixative solution for a period of time to cause the desired fixation of said tissue.

Examples of suitable polymeric materials include polyesters, such as poly(ethylene terephthalate), polylactide, polyglycolide and copolymers thereof; fluorinated polymers, such as polytetrafluoroethylene (PTFE), expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances.

The valve member may also be made of one or more polymers that do not require treatment or modification to be biocompatible. For example, the valve member may include a biocompatible polyurethane. One example of a biocompatible polyurethane, THORALON (THORATEC, Pleasanton, Calif.), has been used in certain vascular applications and is characterized by thromboresistance, high tensile strength, low water absorption, low critical surface tension and good flex life. THORALON and methods of manufacturing this material are disclosed in U.S. Pat. Application Publication No. 2002/0065552 A1 and U.S. Pat. Nos. 4,861,830 and 4,675,361, each of which is incorporated herein by reference in their entirety. Accordingly, THORALON is a polyurethane based polymer (referred to as BPS-215) blended with a siloxane containing surface modifying additive (referred to as SMA-300). Base polymers containing urea linkages can also be used. The concentration of the surface modifying additive may be in the range of 0.5% to 5% by weight of the base polymer.

THORALON can be manipulated to provide either a porous or non-porous material. Formation of porous THORALON is described, for example, in U.S. Pat. No. 6,752,826 and U.S. Pat. Application Publication No. 2003/0149471 A1, both of which are incorporated herein by reference in their entirety. The pores in the polymer may have an average pore diameter from about 1 micron to about 400 microns. Preferably the average pore diameter is from about 1 micron to about 100 microns, and more preferably is from about 1 micron to about 10 microns.

A variety of other biocompatible polyurethanes/polycarbamates and urea linkages (hereinafter "—C(O)N or CON type polymers") may also be employed. Biocompatible CON type polymers modified with cationic, anionic and aliphatic side chains may also be used. See, for example, U.S. Pat. No. 5,017,664, which is incorporated herein by reference in its entirety.

Other biocompatible CON type polymers include: segmented polyurethanes, such as BIOSPAN; polycarbonate urethanes, such as BIONATE; polyetherurethanes, such as ELASTHANE; (all available from POLYMER TECHNOLOGY GROUP, Berkeley, Calif.); siloxane-polyurethanes, such as ELAST-EON 2 and ELAST-EON 3 (AORTECH BIOMATERIALS, Victoria, Australia); polytetramethyleneoxide (PTMO) and polydimethylsiloxane (PDMS) polyether-based aromatic siloxane-polyurethanes, such as PURSIL-10, -20, and -40 TSPU; PTMO and PDMS polyether-based aliphatic siloxane-polyurethanes, such as PURSIL AL-5 and AL-10 TSPU; aliphatic, hydroxy-terminated polycarbonate and PDMS polycarbonate-based siloxane-polyurethanes, such as CARBOSIL-10, -20, and -40 TSPU (all available from POLYMER TECHNOLOGY GROUP). Examples of siloxane-polyurethanes are disclosed in U.S. Pat. Application Publication No. 2002/0187288 A1, which is incorporated herein by reference in its entirety.

In addition, any of these biocompatible CON type polymers may be end-capped with surface active end groups, such as, for example, polydimethylsiloxane, fluoropolymers, polyolefin, polyethylene oxide, or other suitable groups. See, for example the surface active end groups disclosed in U.S. Pat. No. 5,589,563, which is incorporated herein by reference in its entirety.

In some examples, it may be desirable to reinforce a valve member leaflet, for example with threads, fibers, meshes, wires, etc., where additional strength or durability is needed. For example, THORALON leaflets may be reinforced with fibers. The fibers may include any suitable material, but preferably include nanofibers from electrospinning. An electrospun layer of THORALON may be applied to the prosthesis, and further processing may be applied to bring the leaflet construct up to desired specifications.

A valve member may be applied to the prosthetic valve with any suitable attachment mechanism, such as sutures, dipping, adhesives, bonding, tissue welding, barbs or other integral engaging structures along the frame or struts, self-adhesion between regions of the material, chemical adhesion between the valve member and frame, spraying, cross-linking, and the like. The attachment mechanism chosen will depend on the nature of the frame and valve members. For example, the biocompatible polyurethane may be applied as a solution. If necessary, gentle heating and/or agitation, such as stirring, may be employed to cause substantial dissolution. In another example, the valve member may be sewn to struts of the frame.

Graft Material

Also provided are examples wherein the prosthetic valve further comprises a graft material operatively attached to the frame. A wide variety of materials acceptable for use as graft material in implantable medical devices are known in the art, and any suitable material can be utilized. The graft material is preferably a remodelable material and is biocompatible, or able to be made biocompatible.

For example, graft material may include a film, a coating, a sheet of biocompatible fabrics, non-woven materials or porous materials. Examples of biocompatible polymers from which porous sheets can be formed include polyesters, such as poly(ethylene terephthalate), polylactide, polyglycolide and copolymers thereof; fluorinated polymers, such as polytetrafluoroethylene (PTFE), expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. In addition, materials that are not inherently biocompatible may be subjected to surface modifications in order to render the materials biocompatible. Examples of surface modifications include polymerization of biocompatible polymers from the material surface, coating of the surface with a crosslinked biocompatible polymer, and chemical modification with biocompatible functional groups. Thus, any polymer that may be formed into a porous sheet can be used to make a flexible covering, provided the final porous material is biocompatible. Polymers that can be formed into a porous sheet include polyolefins, polyacrylonitrile, nylons, polyaramids and polysulfones, in addition to polyesters, fluorinated polymers, polysiloxanes and polyurethanes as listed above.

Examples of suitable natural graft materials include collagen and extracellular matrix (ECM) material, such as submucosa. One specific example of ECM is small intestine submucose (SIS). In addition to xenogenic biomaterials, such as SIS, autologous tissue can be harvested as well. Additionally Elastin or Elastin Like Polypetides (ELPs) and the like offer potential as a material to fabricate the flexible covering or discrete shaping members to form a device with exceptional biocompatibility. Another alternative is use of allographs such as harvested native valve tissue. Such tissue is commercially available in a cryopreserved state.

Attachment of Prosthetic Valve in Body Vessel

A prosthetic valve may optionally include a means for anchoring the valve within a body vessel. Examples of suitable anchoring means include anchoring elements (e.g., barbs, hooks), suturing, stapling, searing, bonding, adhesives, gluing, or otherwise adhering the medical device to the vessel wall or combinations thereof. For example, the prosthetic valve may be secured in place with one or more anchoring elements.

A wide variety of structural features are acceptable for use in medical devices as anchoring elements, and any suitable structural feature can be used. For example, individual barbs may be used to implant the prosthetic valve into the vessel. The barbs may be secured to the prosthetic valve by any means known to one skilled in the art, including but not limited to welding, stitching, bonding, and adhesives. Desirably, barbs may be attached to the prosthesis frame.

In some examples, the number, arrangement, and configuration of barbs can vary according to design preference and the clinical use of the device. The barbs can have any suitable shape, including points or "fish hook"-like configurations. The barbs may or may not penetrate the vein wall, depending on their design and other factors, including the thickness and type of covering used.

Alternatively or in addition to anchoring elements, bioadhesives may be used for attachment. The bioadhesive can be included in any suitable part of the prosthetic valve. Preferably, the bioadhesive is attached to the abluminal surface of the prosthetic valve. Selection of the type of bioadhesive, the portions of the prosthetic valve comprising the bioadhesive, and the manner of attaching the bioadhesive to the prosthetic valve can be chosen to perform a desired function upon implantation. For example, the bioadhesive can be selected to promote increased affinity of the desired portion of prosthetic valve to the section of the body vessel against which it is urged.

Suitable bioadhesives include, but are not limited to, the following: (1) cyanoacrylates such as ethyl cyanoacrylate, butyl cyanoacrylate, octyl cyanoacrylate, and hexyl cyanoacrylate; (2) fibrinogen, with or without thrombin, fibrin, fibropectin, elastin, and laminin; (3) mussel adhesive protein, chitosan, prolamine gel and transforming growth factor beta(TGF-B); (4) polysaccharides such as acacia, carboxymethyl-cellulose, dextran, hyaluronic acid, hydroxypropyl-cellulose, hydroxypropyl-methylcellulose, karaya gum, pectin, starch, alginates, and tragacanth; (5) polyacrylic acid, polycarbophil, modified hypromellose, gelatin, polyvinylpylindone, polyvinylalcohol, polyethylene glycol, polyethylene oxide, aldehyde relative multifunctional chemicals, maleic anhydride co-polymers, and polypeptides; and (6) any bioabsorbable and biostable polymers derivitized with sticky molecules such as arginine, glycine, and aspartic acid, and copolymers.

Furthermore, commercially available bioadhesives that may be used include, but are not limited to: FOCALSEAL® (biodegradable eosin-PEG-lactide hydrogel requiring photo-polymerization with Xenon light wand) produced by Focal; BERIPLAST® produced by Adventis-Bering; VIVOSTAT® produced by ConvaTec (Bristol-Meyers-Squibb); SEALAGEN™ produced by Baxter; FIBRX® (containing virally inactivated human fibrinogen and inhibited-human thrombin) produced by CryoLife; TISSEEL® (fibrin glue composed of plasma derivatives from the last stages in the natural coagulation pathway where soluble fibrinogen is converted into a solid fibrin) and TISSUCOL® produced by Baxter; QUIXIL® (Biological Active Component and Thrombin) produced by Omrix Biopharm; a PEG-collagen conjugate produced by Cohesion (Collagen); HYSTOACRYL® BLUE (ENBUCRILATE) (cyanoacrylate) produced by Davis & Geck; NEXACRYL™ (N-butyl cyanoacrylate), NEXABOND™, NEXABOND™ S/C, and TRAUMASEAL™ (product based on cyanoacrylate) produced by Closure Medical (TriPoint Medical); DERMABOND® which consists of 2-octyl cyanoacrylate produced as DERMABOND® by (Ethicon); TISSUEGLU® produced by Medi-West Pharma; and VETBOND® which consists of n-butyl cyanoacrylate produced by 3M.

Bioactive Agents

Optionally, the prosthetic valve can include one or more bioactive agents. The bioactive agent can be included in any suitable part of the prosthetic valve. Selection of the type of bioactive, the portions of the prosthetic valve comprising the bioactive agent, and the manner of attaching the bioactive agent to the prosthetic valve can be chosen to perform a desired function upon implantation. For example, the bioactive material can be selected to treat indications such as vascular graft stenosis.

The bioactive materials can be attached to the prosthetic valve in any suitable manner. For example, a bioactive agent can be combined with a biocompatible polyurethane, impregnated in the valve members, positioned within or on a graft material, or attached to the surface of the prosthetic valve.

The bioactive agent can be selected to perform one or more desired biological functions. For example, the abluminal surface of the prosthetic valve can comprise a bioactive selected to promote the ingrowth of tissue from the interior wall of a body vessel, such as a growth factor. An anti-angiogenic or antneoplastic bioactive such as paclitaxel, sirolimus, or a rapamycin analog, or a metalloproteinase inhibitor such as batimastaat can be incorporated in or coated on the frame or graft material to mitigate or prevent undesired conditions in the vessel wall, such as restenosis. Many other types of bioactive agents can be incorporated in the prosthetic valve.

Bioactive materials for use in biocompatible coatings include those suitable for coating an implantable medical device. The bioactive agent can include, for example, one or more of the following: antiproliferative agents (sirolimus, paclitaxel, actinomycin D, cyclosporine), immunomodulating drugs (tacrolimus, dexamethasone), metalloproteinase inhibitors (such as batimastat), antisclerosing agents (such as collagenases, halofuginone), prohealing drugs (nitric oxide donors, estradiols), mast cell inhibitors and molecular interventional bioactive agents such as c-myc antisense compounds, thromboresistant agents, thrombolytic agents, antibiotic agents, anti-tumor agents, antiviral agents, anti-angiogenic agents, angiogenic agents, anti-mitotic agents, anti-inflammatory agents, angiostatin agents, endostatin agents, cell cycle regulating agents, genetic agents, including hormones such as estrogen, their homologs, derivatives, fragments, pharmaceutical salts and combinations thereof. Other useful bioactive agents include, for example, viral vectors and growth hormones such as Fibroblast Growth Factor and Transforming Growth Factor-β.

Prosthetic valves comprising an antithrombogenic bioactive agent are particularly preferred for implantation in areas of the body that contact blood. For example, an antithrombogenic bioactive agent can be coated on the valve member surface. An antithrombogenic bioactive agent is any bioactive agent that inhibits or prevents thrombus formation within a body vessel. The prosthetic valve can comprise any suitable antithrombogenic bioactive agent. Types of antithrombotic bioactive agents include anticoagulants, antiplatelets, and fibrinolytics. Anticoagulants are bioactive materials which act on any of the factors, cofactors, activated factors, or activated cofactors in the biochemical cascade and inhibit the synthesis of fibrin. Antiplatelet bioactive agents inhibit the adhesion, activation, and aggregation of platelets, which are key components of thrombi and play an important role in thrombosis. Fibrinolytic bioactive agents enhance the fibrinolytic cascade or otherwise aid in dissolution of a thrombus. Examples of antithrombotics include but are not limited to anticoagulants such as thrombin, Factor Xa, Factor VIIa and tissue factor inhibitors; antiplatelets such as glycoprotein IIIb/IIIa, thromboxane A2, ADP-induced glycoprotein IIb/IIIa, and phosphodiesterase inhibitors; and fibrinolytics such as plasminogen activators, thrombin activatable fibrinolysis inhibitor (TAFI) inhibitors, and other enzymes which cleave fibrin.

Further examples of antithrombotic bioactive agents include anticoagulants such as heparin, low molecular weight heparin, covalent heparin, synthetic heparin salts, coumadin, bivalirudin (hirulog), hirudin, argatroban, ximelagatran, dabigatran, dabigatran etexilate, D-phenalanyl-L-poly-L-arginyl, chloromethy ketone, dalteparin, enoxaparin, nadroparin, danaparoid, vapiprost, dextran, dipyridamole, omega-3 fatty acids, vitronectin receptor antagonists, DX-9065a, CI-1083, JTV-803, razaxaban, BAY 59-7939, and LY-51,7717; antiplatelets such as eftibatide, tirofiban, orbofiban, lotrafiban, abciximab, aspirin, ticlopidine, clopidogrel, cilostazol, dipyradimole, nitric oxide sources such as sodium nitroprussiate, nitroglycerin, S-nitroso and N-nitroso compounds; fibrinolytics such as alfimeprase, alteplase, anistreplase, reteplase, lanoteplase, monteplase, tenecteplase, urokinase, streptokinase, or phospholipid encapsulated microbubbles; and other bioactive agents such as endothelial progenitor cells or endothelial cells.

Also particularly preferred are prosthetic valves comprising a thrombolytic bioactive agent. Desirably, the thrombolytic bioactive agent is positioned on the luminal surface of the prosthetic valve or within the valve members. Thrombolytic agents are used to dissolve blood clots that may adversely affect blood flow in body vessels. A thrombolytic agent is any therapeutic agent that either digests fibrin fibres directly or activates the natural mechanisms for doing so. The prosthetic valve can comprise any suitable thrombolytic agent. Examples of commercial thrombolytics, with the corresponding active agent in parenthesis, include, but are not limited to, Abbokinase (urokinase), Abbokinase Open-Cath (urokinase), Activase (alteplase, recombinant), Eminase (anitstreplase), Retavase (reteplase, recombinant), and Streptase (streptokinase). Other commonly used names are anisoylated plasminogen-streptokinase activator complex; APSAC; tissue-type plasminogen activator (recombinant); t-PA; rt-PA.

A bioactive agent can be incorporated in or applied to portions of the prosthetic valve by any suitable method that permits adequate retention of the bioactive agent material and the effectiveness thereof for an intended purpose upon implantation in the body vessel. The configuration of the bioactive agent on or in the prosthetic valve will depend in part on the desired rate of elution for the bioactive agent. Bioactive agents can be coated directly on the prosthetic valve surface or can be adhered to a prosthetic valve surface by means of a coating. For example, an antithrombotic bioactive agent can be blended with a polymer and spray or dip coated on the device surface. For example, a bioactive agent material can be posited on the surface of the prosthetic valve and a porous coating layer can be posited over the bioactive agent material. The bioactive agent material can diffuse through the porous coating layer. The coating layer can also be nonporous wherein the rate of diffusion of the bioactive agent material through the coating layer is controlled by the rate of dissolution of the bioactive agent material in the coating layer.

Delivery of Prosthetic Valves

Prosthetic valves may be configured for intraluminal delivery to a body vessel. For example, a prosthetic valve may preferably be compressed to a delivery configuration within a retaining sheath that is part of a delivery system, such as a catheter-based system. Upon delivery, the prosthetic valve can be expanded, for example, by inflating a balloon from inside the prosthetic valve. The delivery configuration can be maintained prior to deployment of the prosthetic valve by any suitable means, including a sheath, a suture, a tube or other restraining material around all or part of the compressed prosthetic valve, or other methods.

Prosthetic valves can be deployed in a body lumen by any means appropriate to their design. The prosthetic valves can be adapted for deployment using conventional methods and employing percutaneous transluminal catheter devices. The prosthetic valves are designed for deployment by any of a variety of in situ expansion means.

In one example, the prosthetic valve may be mounted onto a catheter that holds the prosthesis as it is delivered through the body lumen and then releases the prosthetic valve and allows it to self-expand into contact with the body lumen. This deployment is effected after the prosthetic valve has been introduced percutaneously, transported transluminally and positioned at a desired location by means of the catheter. The self-expanding prosthetic valve may be deployed according to well-known deployment techniques for self-expanding medical devices. For example, the prosthesis may be positioned at the distal end of a catheter with a removable sheath or sleeve placed over the prosthetic valve to hold the prosthetic valve in a contracted state with a relatively small diameter. The prosthetic valve may then be implanted at the point of treatment by advancing the catheter over a guidewire to the location of the lesion and then withdrawing the sleeve from over the prosthesis. The prosthetic valve will automatically expand and exert pressure on the wall of the blood vessel at the site of the lesion. The catheter, sleeve, and guidewire may then be removed from the patient.

In some examples, a bioabsorbable suture or sheath can be used to maintain a self-expanding prosthetic valve in a compressed configuration both prior to and after deployment. As the bioabsorbable sheath or suture is degraded by the body after deployment, the prosthetic valve can expand within the body vessel. In some examples, a portion of the prosthesis can be restrained with a bioabsorbable material and another portion allowed to expand immediately upon implantation. For example, a self-expanding frame can be partially restrained by a bioabsorbable material upon deployment and later expand as the bioabsorbable material is absorbed.

In another example, the prosthetic valve is first positioned to surround a portion of an inflatable balloon catheter. The prosthetic valve, with the balloon catheter inside is configured at a first, collapsed diameter. The prosthesis and the inflatable balloon are percutaneously introduced into a body lumen, following a previously positioned guidewire. For example, in rapid exchange, a rapid exchange prosthesis delivery balloon catheter allows exchange from a balloon angioplasty catheter to a prosthesis delivery catheter without the need to replace the angioplasty catheter guide wire with an exchange-length wire guide before exchanging the catheters. The prosthesis may be tracked by a fluoroscope, until the balloon portion and associated prosthetic valve are positioned within the body passageway at the point where the prosthesis is to be placed. Thereafter, the balloon is inflated and the prosthesis is expanded by the balloon portion from the collapsed diameter to a second expanded diameter. After the prosthetic valve has been expanded to the desired final expanded diameter, the balloon is deflated and the catheter is withdrawn, leaving the prosthetic valve in place. The prosthetic valve may be covered by a removable sheath during delivery to protect both the prosthesis and the vessels.

While the terms "contracted" and "compressed" have been used to describe the prosthetic valve as having the small diameter necessary for delivery to an implantation site, it will be appreciated that the terms, especially as applied to pressure-expandable prosthetic valves, should not be used to imply that the medical device is under external pressure to provide the medical device with a small diameter; i.e., a "contracted" or "compressed" pressure-expandable prosthetic valve may be formed and naturally reside in the "contracted" or "compressed" state until internally pressurized to expand. Therefore, "contracted" and "compressed" are intended only to imply that the prosthetic valve is in a state of having a small diameter relative to an expanded state.

Methods for delivering a prosthetic valve as described herein to any suitable body vessel are also provided, such as a vein, artery, biliary duct, ureteral vessel, body passage or portion of the alimentary canal.

Methods of Treatment and Prevention

Still other aspects provide methods of treating a subject, which can be animal or human, comprising the step of providing one or more prostheses attached to one or more valve members, as described herein. In some aspects, methods of treatment may also provide the step of delivering a prosthetic valve to a point of treatment in a body vessel, or deploying a prosthetic valve at the point of treatment, wherein the prosthetic valves are as described herein.

In one example the method comprises a step of delivering a prosthetic valve as described herein to a point of treatment in a body vessel, and deploying the prosthesis at the point of treatment. The delivering step can comprise delivery by surgical or by percutaneous delivery techniques known to those skilled in the art.

Methods for treating and/or preventing certain conditions are also provided, such as venous valve insufficiency, varicose veins, esophageal reflux, restenosis or atherosclerosis. In some examples, the disclosure relates to methods of treating venous valve-related conditions, such as venous valve insufficiency and varicose veins. A "venous valve related condition" refers to any condition presenting symptoms that can be diagnostically associated with improper function of one or more venous valves. In mammalian veins, natural valves are positioned along the length of the vessel in the form of leaflets disposed annularly along the inside wall of the vein which open to permit blood flow toward the heart and close to prevent back flow. These natural venous valves act as open to permit the flow of fluid in the desired direction, and close upon a change in pressure, such as a transition from systole to diastole. When blood flows through the vein, the pressure forces the valve leaflets apart as they flex in the direction of blood flow and move towards the inside wall of the vessel, creating an opening therebetween for blood flow. Functioning leaflets return to a closed position to restrict or prevent blood flow in the opposite, i.e. retrograde, direction after the pressure is relieved. The leaflets, when functioning properly, extend radially inwardly toward one another such that the tips contact each other to block backflow of blood. Two examples of venous valve related conditions are chronic venous insufficiency and varicose veins.

On occasion, and for a variety of reasons, such as congenital valve or vein weakness, disease in the vein, obesity, pregnancy, and/or an occupation requiring long periods of standing, one or more valves in a vein will allow deleterious retrograde flow to occur. When a valve allows such retrograde flow, blood may collect, or pool, in vessels beneath the valve. This pooling of blood can cause an increase in the venous pressure below the valve. Venous valves that allow such deleterious retrograde flow are known as incompetent or inadequate venous valves. The condition resulting from such incompetent venous valves is known as venous valve insufficiency. In the condition of venous valve insufficiency, the venous valve leaflets do not function properly. Incompetent venous valves can cause the veins to bulge, can cause swelling in the patient's lower extremities, and can result in varicose veins and/or chronic venous insufficiency. If left untreated, venous valve insufficiency can cause venous stasis ulcers of the skin and subcutaneous tissue.

Accordingly, methods of treating a venous valve related condition may comprise the step of providing one or more medical devices comprising implantable frames and/or valve prostheses as described herein. Methods of treatment may comprise the step of providing one or more frames attached to one or more valve leaflets. In some examples, methods of treatment may also include the steps of delivering a medical device to a point of treatment in a body vessel, and deploying a medical device at the point of treatment, wherein the medical devices are as described herein. Such medical devices can be inserted intravascularly, for example from an implantation catheter. The medical devices can function as a replacement venous valve, or enhance venous valve function by bringing incompetent valve leaflets into closer proximity. In one procedure, venous valve function can be provided by an implanted medical device.

In accordance with certain methods of treatment, a medical device comprising an implantable frame may be placed in a human leg having greater saphenous vein (GSV) and femoral vein which adjoin at the sapheno-femoral junction. Preferably, the medical device is implanted within the GSV near the medial side of the knee and a point prior to the sapheno-femoral junction. Desirably, the medical device functions as a valve to prevent or reduce reflux of venous blood from the sapheno-femoral junction in a direction down toward the medial side of the knee. Such occlusion may be effective to treat varicosities that commonly occur in lower portions of the leg, e.g. portions occurring below the knee. The medical device is preferably implanted from a delivery catheter via percutaneous access to the GSV, for example by the Seldinger technique or any other suitable technique. For instance, an access needle can be passed through the skin to access the GSV, and a wire guide can be passed through the access needle and into the vein. Prior to deployment of an inverted occlusion device, wire guide can be used for any number of conventional procedures including catheterization and imaging procedures in order to locate the sapheno-femoral junction. After any such preliminary procedures that are performed, the wire guide can be used in a deployment procedure for an inflatable occlusion device.

One preferred method of treating a venous valve-related condition by deploying a valve prosthesis within a body vessel, the method comprising the steps of: inserting valve prosthesis into a body vessel in a radially compressed configuration, advancing the valve prosthesis within a body vessel; positioning the valve prosthesis at a point of treatment within the body vessel; and expanding the valve prosthesis from the compressed configuration to the expanded configuration to deploy the valve prosthesis within the body vessel, the expanded valve prosthesis laterally distending up to one half of the circumference of the body vessel. The valve prosthesis may include: a frame moveable from the compressed configuration to an expanded configuration, the frame defining an interior lumen and having a proximal end, a distal end, a luminal surface, and an abluminal surface; the frame defining a laterally asymmetric partial sinus portion of the interior lumen when the frame is in the expanded configuration; and a means for regulating fluid flow through the interior lumen positioned within the interior lumen and being attached to the frame. The means for regulating fluid flow through the interior lumen may be a monocuspid valve leaflet having a base attached to the frame and a flexible free edge distal to the base, the free edge adapted to form a valve orifice moveable within the interior lumen to modify fluid flow therethrough by moving between an open configuration permitting fluid flow through the valve orifice and a closed configuration engaging a portion of the frame opposite the partial sinus portion to reduce fluid flow through the lumen.

While various aspects and examples have been described, it will be apparent to those of ordinary skill in the art that many more examples and implementations are possible within the scope of the disclosure. Accordingly, the invention is not to be restricted except in light of the attached claims and their equivalents.

The invention claimed is:

1. A valve prosthesis for implantation in a body vessel having a vessel wall, said valve prosthesis comprising:
an implantable frame radially-expandable from a compressed configuration to an expanded configuration having an interior lumen, the frame defining a laterally asymmetric partial sinus portion of the interior lumen extending around between about 10% and about 90% of the circumference of the frame in the expanded configuration; and
a valve member;
wherein the frame includes a proximal portion, a distal portion, and an intermediate portion;
the valve member comprising at least one leaflet operatively attached to the frame, the at least one leaflet having a base and a free edge and being movable between a first position to permit fluid flow through said body vessel in a first direction and a second position to form a valve pocket that collects fluid and substantially prevents fluid flow through said body vessel in a second direction that is opposite the first direction;
the partial sinus portion of the interior lumen being defined by a bulge of the intermediate portion in a lateral direction such that the bulge of the intermediate portion has a width greater than the width of the distal portion and the proximal portion;
wherein the at least one leaflet forms a seal with a first portion of said vessel wall opposite the bulge of the intermediate portion of the frame and cooperatively defines the valve pocket with a second portion of said vessel wall of said body vessel adjacent the bulge of the intermediate portion when the at least one leaflet is in the second position.

2. The prosthesis of claim 1, where the proximal portion and the distal portion have a radial force that is less than the radial force of the intermediate portion.

3. The prosthesis of claim 1, where the intermediate portion has a longitudinal length at least as great as the longitudinal length of the at least one leaflet.

4. The valve prosthesis of claim 1, the leaflet free edge defining a valve orifice moveable within the interior lumen to modify fluid flow through the interior lumen by movement of the free edge between an open position permitting fluid flow through the valve orifice and a closed position engaging a portion of the frame opposite the partial sinus portion of the interior lumen to reduce fluid flow through the interior lumen.

5. The valve prosthesis of claim 4, where in the open position the valve leaflet is at least partially within the partial sinus.

6. The valve prosthesis of claim 1, where the partial sinus portion extends around between about 25% and about 75% of the circumference of the frame in the expanded configuration.

7. The valve prosthesis of claim 1, where the partial sinus portion extends around between about 40% and 60% of the circumference of the frame in the expanded configuration.

* * * * *